US00PP28018P3

(12) United States Plant Patent
Olesen

(10) Patent No.: US PP28,018 P3
(45) Date of Patent: May 16, 2017

(54) MINIATURE ROSE PLANT NAMED 'POULPAR085'

(50) Latin Name: *Rosa hybrid*
Varietal Denomination: Poulpar085

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 14/756,264

(22) Filed: Aug. 20, 2015

(65) Prior Publication Data

US 2017/0055394 P1 Feb. 23, 2017

(51) Int. Cl.
*A01H 5/02* (2006.01)

(52) U.S. Cl.
USPC ..... Plt./122

(58) Field of Classification Search
USPC ..... Plt./122
See application file for complete search history.

(56) References Cited

PUBLICATIONS

Indoor Roses by Poulsen Main Varieties 2013.*
PLUTO Plant Variety Database Aug. 10, 2016.*

* cited by examiner

*Primary Examiner* — Annette Para

(57) ABSTRACT

A new garden rose plant of the miniature class which has abundant, red and white bicolor flowers and attractive foliage. This new and distinct variety has shown to be uniform and stable in the resulting generations from asexual propagation.

1 Drawing Sheet

Botanical designation: *Rosa* hybrid.
Variety denomination: 'Poulpar085'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2008 and the resulting seeds were planted in a controlled environment in Fredensborg, Denmark. The new variety, named 'Poulpar085', originated as a single seedling from the stated cross.

The new variety may be distinguished from its male pollen parent and female seed parent primarily by the following characteristics. The female seed parent has flowers which are a blend of red and yellow-orange, while the new variety has flowers which are red with white striped. The male pollen parent has flowers which are deep yellow.

The objective of the hybridization of this rose variety was to create a new and distinct variety for garden use with unique qualities, such as:

1. Uniform and abundant red and white bicolor flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpar085' from all other varieties of which we are aware.

As part of the rose development program, Mogens N. Olesen germinated the seeds from the aforementioned hybridization during winter of 2008 and conducted evaluations on the resulting seedlings in a controlled environment in Fredensborg, Denmark. 'Poulpar085' was selected in the spring of 2009 by the inventor as a single plant from the progeny of the aforementioned hybridization.

Asexual reproduction of 'Poulpar085' by traditional budding and rooted cuttings was first done by Mogens N. Olesen in the nursery in Fredensborg, Denmark in July, 2009. This initial and other subsequent asexual propagations conducted in controlled environments have demonstrated that the characteristics of 'Poulpar085' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpar085'. Specifically illustrated are open flowers, flower petals detached, a cluster of flower buds on a branch, leaves, petiole, and sepals detached. Plants shown are 1 year old.

DETAILED DESCRIPTION OF THE VARIETY

The following is a description of 'Poulpar085',as observed in its growth in in a field nursery in Marion County, Oreg. Observed plants are 1 year old, and were grown on their own roots. Color references are made using The Royal Horticultural Society (London, England) Colour Chart, 2001, except where common terms of color are used.

For a comparison, several physical characteristics of the rose variety 'Poulpah024', United States Plant Patent Number are compared to 'Poulpar085' in Chart 1.

CHART 1

| | 'Poulpar085' | 'Poulpah024' |
|---|---|---|
| Petal Count | 70 | 90 |
| Flower Diameter | 50 to 60 mm | 55 to 60 |
| Color of petal upper surface after opening, outermost. | Red-Purple Group 60A splashed with Red-Purple Group 62C | Red-Purple Group 57A to 58B with streaks of White Group 155B and or Yellow Group 5D layered over |

FLOWER AND FLOWER BUD

Blooming habit: Continuous.

Flower bud:

*Size.*—Upon opening, 20 mm in length from base of receptacle to end of bud. Bud diameter is 10 mm.

*Bud form.*—Ovoid.

*Bud color.*—As sepals divide petals are Red-Purple Group 60A and 60C.

*Sepal inner surface.*—Color: Yellow-Green Group 147C. Surface: Lightly pubescent.

*Sepal outer surface.*—Color: Yellow-Green Group 144A with intonations of Greyed-Red Group 180A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—20 to 25 mm long, 7 mm wide.

*Receptacle.*—Texture: Smooth. Size: 5 mm in height, 6 mm wide. Color: Yellow-Green Group 144A. Shape: Campanulate.

*Pedicel.*—Surface: Smooth. Length: 25 to 35 mm. Diameter: 2.5 mm on average. Color: Yellow-Green Group 144B with intonations of Greyed-Red Group 180B. Strength: Moderate.

*Peduncle.*—Length: 1 to 8 cm. Diameter: About 3 mm. Color: Green Group 138A. Texture: Smooth.

Flower bud development: Flower buds are borne in clusters of 3 to 9 flower buds per stem.

Flower bloom:

*Fragrance.*—None.

*Duration.*—The blooms have a duration on the plant of approximately 20 days. Petals do not fall cleanly away from plant after flowers have fully matured.

*Size.*—Flower diameter is 50 to 60 mm when open. Flower depth is 25 mm.

*Flower shape.*—Rosette Very double flower with many slightly overlapping petals of different sizes.

*Shape of flower, side view.*—The upper portion is flattened convex. The lower portion is concave.

Petalage: Under normal conditions, flowers have 70 petals total.

General tonality of flower: Open flowers are Red-Purple Group 60A.

Petal color:

*Upon opening, inner and outer petals.*—Upper surface: Red-Purple Group 60A splashed with Red-Purple Group 62C. Lower surface: Red-Purple Group 60A splashed with Red-Purple Group 62C.

*Basal petal spots, upon opening.*—Upper surface: White Group N155B, occasionally Yellow Group 3C. Lower surface: White Group N155B, occasionally Yellow Group 3D.

*After opening, inner and outer petals.*—Upper surface: Red-Purple Group 60A splashed with Red-Purple Group 62C. Lower surface: Red-Purple Group 60A splashed with Red-Purple Group 62C.

*Basal petal spots, after opening.*—Upper surface: White Group N155B, occasionally Yellow Group 3C. Lower surface: White Group N155B, occasionally Yellow Group 3D.

Petals:

*Petal reflex.*—Weak.

*Margin.*—Entire and uniform. Occasional point at the apex.

*Shape.*—Generally ovate. Apex shape: Rounded. Base shape: Acute.

*Size.*—20 mm (l)×20 mm (w).

*Texture.*—Smooth.

*Thickness.*—Average.

Petaloids:

*Size.*—About 9 mm (l) by 6 mm (w).

*Quantity.*—5 to 10.

*Shape.*—Apex is rounded, sometimes acute. The base is acute.

*Color of petaloids.*—Upper surface: Red-Purple Group 60A splashed with Red-Purple Group 62C. Lower surface: Red-Purple Group 60A splashed with Red-Purple Group 62C. Basal petaloid spots: Upper surface: White Group N155B, occasionally Yellow Group 3C. Lower surface: White Group N155B, occasionally Yellow Group 3D.

Reproductive flower parts:

*Pollen.*—None observed.

*Anthers.*—Size: 2 mm in length. Color: Yellow Group 7A. Quantity: 30 on average.

*Filaments.*—Color: Orange Group 25A. Length: 2 to 4 mm.

*Pistils.*—Length: 5 mm. Quantity: 15 on average.

*Stigmas.*—Color: Yellow Group 10B.

*Styles.*—Color: Greyed-Orange Group 177B.

*Location of stigmas.*—Superior in location relative to the length of the filaments and the height of the anthers.

*Hips.*—None Observed.

PLANT

Plant growth: Upright, bushy. Plants are 30 to 40 cm in height, and 30 cm wide.

Stems:

*Color.*—Juvenile growth: Yellow-Green Group 144B. Mature growth: Yellow-Green Group 144A.

*Length.*—On average, canes are 30 cm from the base of the plant to the flowering portion.

*Diameter.*—4 mm.

*Internodes.*—On mature canes about 28 mm between nodes.

*Surface texture.*—Young wood: Smooth. Older wood: Smooth.

Long prickles: None observed.

Plant foliage:

*Compound leaf.*—120 mm (l)×75 (w).

*Quantity.*—3 leaves per 10 cm of stem on average.

*Leaf bearing angle to the stem.*—45 degrees.

*Color of juvenile foliage*.—Upper side: Yellow-Green Group 146A. Lower side: Green Group 138B. Anthocyanin: Greyed-Purple Group 185B at margins.

*Color of mature foliage*.—Upper side: Yellow-Green Group 147A. Lower side: Yellow-Green Group 147C.

Plant leaves and leaflets:

*Stipules*.—Size: 8 to 10 mm long, 2 mm wide. Quantity: 2 per compound leaf. Shape: Linear, slightly broad based with outward extending apices. Margins: Finely serrated. Color:

*Petiole*.—Length: 15 mm. Diameter: 2 mm.

*Upper surface*.—Color: Yellow-Green Group 146B.

*Lower surface*.—Color: Yellow-Green Group 144A.

*Rachis*.—Length: 20 mm. Upper surface: Color: Yellow-Green Group 146B.

*Lower surface*.—Color: Yellow-Green Group 144A. Observations: Small prickles.

*Leaflet*.—Quantity: Normally 5 leaflets. Margins: Serrated. Size: On average terminal leaflets are 50 mm long, 30 mm wide. Shape: Generally elliptical. Base: Rounded. Apex: Acute to mucronate. Texture: Smooth. Thickness: Average. Arrangement: Odd pinnate. Venation: Reticulate. Glossiness: Not glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the miniature rose class named 'Poulpar085', substantially as illustrated and described herein, due to its abundant red and white bicolor flowers, disease resistance, and extended period of bloom.

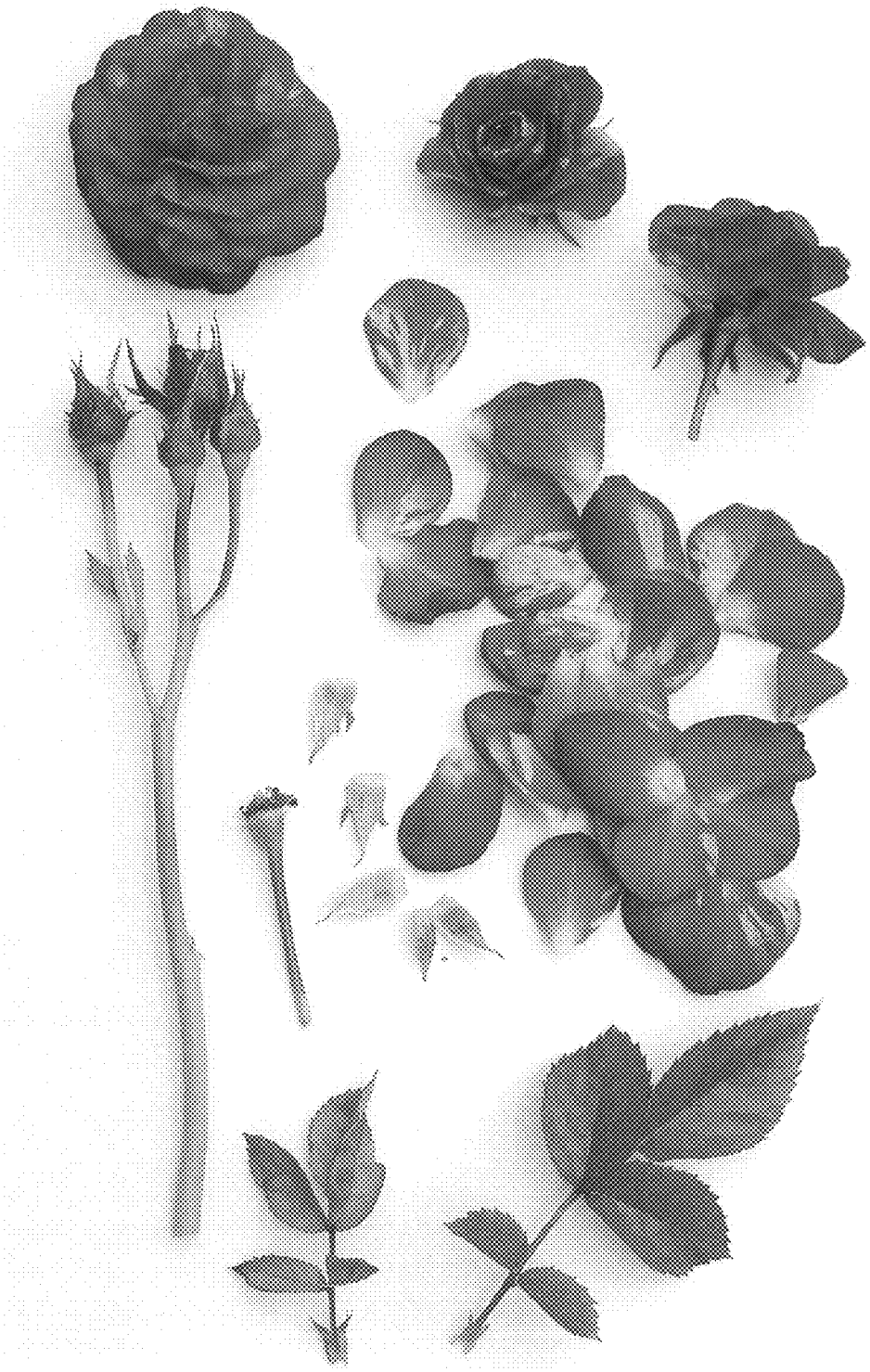

* * * * *